(12) United States Patent
Lahanas et al.

(10) Patent No.: US 6,290,941 B1
(45) Date of Patent: Sep. 18, 2001

(54) POWDER TO LIQUID COMPOSITIONS

(75) Inventors: Konstantinos M. Lahanas, Paramus, NJ (US); Nicolae Vrabie, Jackson Heights, NY (US); Erlinda Santos, Queens Village, NY (US); Saul Miklean, Floral Park, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/447,909

(22) Filed: Nov. 23, 1999

(51) Int. Cl.⁷ ............................ A61K 7/035; A61K 7/00
(52) U.S. Cl. .................... 424/69; 424/401; 424/489; 424/490; 424/497
(58) Field of Search ................ 424/401, 69, 489, 424/490, 497

(56) References Cited

U.S. PATENT DOCUMENTS 4,777,035  10/1988  Shin .................................. 424/66

FOREIGN PATENT DOCUMENTS

| 0855177 A2 | 7/1998 | (EP) | ............ A61K/007/035 |
| 58039609 * | 3/1983 | (JP) | . |
| 5065212 | 3/1993 | (JP) | . |
| 6-166611 | 6/1994 | (JP) | ............ A61K/007/02 |
| 6-211620 | 8/1994 | (JP) | ............ A61K/007/00 |
| 8-092036 | 4/1996 | (JP) | ............ A61K/007/025 |

* cited by examiner

*Primary Examiner*—Shelley A. Dodson
*Assistant Examiner*—Konata M. George
(74) *Attorney, Agent, or Firm*—Kenyon & Kenyon

(57) ABSTRACT

The invention relates to cosmetic or pharmaceutical powder-to-liquid compositions comprising hydrophobically coated silica particles into which are incorporated water and a water soluble polymer, the composition containing substantially no oil.

23 Claims, No Drawings

POWDER TO LIQUID COMPOSITIONS

FIELD OF THE INVENTION

The present invention relates to cosmetic and pharmaceutical compositions. More specifically, the invention relates to powder compositions that convert to liquid on the skin.

BACKGROUND OF THE INVENTION

Powder cosmetic and skin care compositions are well-known and widely used for a variety of purposes. Normally, they are composed of a combination of different types of small particles that perform a number of different functions in the products in which they are used, and can particularly contribute to ease of application of pigments to the face. For this reason, powders are particularly favored in color cosmetics for eyeshadows, blushers, and eyebrow products; however, they are also used widely in personal care products as dusting and baby powders, for foot care and hair care, and as a base for a variety of medicated products. From a functional point of view, one of their major advantages is their ability to absorb water, thereby assisting in drying damp or perspiring skin, as well as being able to absorb excess sebum from the skin or hair. Although widely used, and largely effective for the intended purposes, there are some drawbacks to the use of powder. By nature, powders tend to scatter, and may not remain in place after application. In addition, one of their main advantages, the ability to absorb moisture, contributes to one of their main disadvantages: a majority of powders are entirely or largely composed of anhydrous elements, and in the course of absorbing moisture, can cause discomfort to the skin that is already very dry if used frequently.

Recent changes in powder technology have produced powders that contain substantial amounts of water(JP 58039609; JP 5065212). These products look and feel like standard powders before application, and are applied to the skin in the same way as standard powders. However, once they are rubbed or pressed onto the skin, they become liquid, thereby ensuring that the product remains in place, and also delivering moisture, rather than withdrawing it. These powder-to-liquid products rely largely on the presence of porous hydrophobic silica beads to hold the water that is released on application. These silica beads are themselves very gritty and dry, and ordinarily need to be used at a fairly high level to achieve the required water retention before application. Therefore, in order to compensate for the unpleasant feel of the silica, the formula usually contains a substantial amount of oil or other lubricants. Clearly, the presence of oil in the formula tends to counteract the desired effect of the oil absorption by the powder, thereby defeating at least one purpose of the product. Therefore, there continues to be a need for a powder composition that delivers moisture to the skin, yet achieves a smooth, non-gritty feel on the skin without the necessity of the addition of oil to the product or to the skin.

SUMMARY OF THE INVENTION

The invention provides a powder composition that is converted to liquid when applied to the skin. The compositions comprises hydrophobically-coated porous silica into which is incorporated an aqueous phase comprising water and a water-soluble polymer. In a preferred embodiment, the powder contains substantially no oil, and the aqueous phase contains one or more water-soluble actives. The powder compositions of the invention have the valuable property of being able to deliver a variety of water soluble actives in powder form, have a smooth, cooling feeling when applied to the skin, and avoiding some of the problems associated with other types of powders which may frequently contain oil.

DETAILED DESCRIPTION OF THE INVENTION

The compositions of the invention are prepared as loose powder compositions containing fairly high levels of water; upon application and rubbing of the powder on the skin, the composition releases water, and becomes liquid on the skin. Such a product is quite versatile, in that it provides the advantages of a powder, such as portability and ease of application, the feeling of dryness upon initial application on the skin in hot weather, and absorption of oils by the contained powders. However, it has the added advantage of containing a large quantity of water, which permits the delivery of valuable water soluble actives, and also provides a burst of cool moisture when rubbed into the skin.

Powder-to-liquid compositions are known in the art, as noted above, and many are based on the use of porous silica particles to hold the water phase of the composition. The more silica particles present, the more water the composition can hold. However, silica particles, when present in large quantities, confer a dry and gritty feeling on the skin. Thus, previous such compositions relied on the addition of oil to the composition to mask the unpleasant feeling of the silica as it is applied. Like the prior art products, the base for the powder compositions of the present invention are also water-absorbing porous spherical silica materials, preferably a fumed silica. However, as shown below, the nature of the water phase of the present compositions differs from those previously known in such a way as to allow reduction of the amount of silica to relatively low levels, while retaining the water-holding capacity, and permitting substantial elimination of added oil from the formula.

Preferably, the porous silica materials used in the compositions are hydrophobically coated. The hydrophobic coating may be any which is typically used for such purposes, e.g., a hydrocarbon or silicone coating, and preferably is one that is covalently bonded to the particle. In a preferred embodiment, the silica is coated with a silicone-based coating, such as an organosiloxane or polysiloxane or a silicone oil. The particle size is preferably about 0.01–40$\mu$, more preferably about 0.01–20$\mu$, and most preferably about 0.01–10$\mu$. Examples of suitable coated particles are trimethyl silylate-coated silica, dimethyl silylate coated silica, octyl silylate-coated silica, or silicone oil-coated silica. Preferred particles are trimethyl silylate-coated silica, commercially available from Cabot. The silica particles normally constitute from about 0.05 to about 10%, preferably about 0.1 to about 5%, more preferably about 0.25 to about 3%, and most preferably below 3%, by weight of the total composition.

In the powder form, occupying the pores of the silica particles is an aqueous phase, the basis of generating the liquid form of the composition. The aqueous phase may be any cosmetically acceptable water-based material, such as deionized water, or a floral water, or any water miscible liquids, such as alcohols. The water and/or water miscible liquids will normally constitute from about 50 to about 90%, preferably about 60 to about 80%, by weight of the total composition. The aqueous phase of the present composition is unique, in the presence of highly absorbent water-soluble polymers. The polymers employed can be any substantially surfactant-free, water-soluble polymer, such as homo- and copolymers of vinyl pyrrolidone, e.g., PVP, or PVP/PVA copolymer, homo-or copolymers of vinyl alcohol, such as polyvinyl alcohol, homo-or copolymers of acrylic and/or methacrylic acids, and salts and esters thereof, cellulosic polymers, polyethylene glycols and polyurethanes. Preferred are acrylate polymers and copolymers, particularly sodium polyacrylate. The water-soluble polymer is used in the water phase in an amount of from about 0.01 to about 5%, preferably about 0.1 to about 3%, most preferably about 0.1 to about 1%, by weight of the total composition. The use of the water-soluble, highly absorbent polymer, permits the retention of larger amounts of water within a smaller quantity of silica particles than would otherwise be possible, thereby reducing the unpleasant effect of the silica particles on the skin.

Another important aspect of the water phase is the ability to deliver water-soluble actives or skin-conditioning agents to the skin in an initial powder form. Any water-soluble active component can be added to the water phase of the composition. Examples of useful materials include, but are not limited to, humectants, such as hyaluronic acid, water-soluble vitamins, such as Vitamin C, antiperspirant/deodorant compounds or complexes, such as aluminum zirconium tetrachlorohydrex gly, aluminum chloride, aluminum chlorohydrate, and aluminum chlorohydrex PG; water soluble preservatives and antioxidants; hydrogels; glycerol; elastin; collagen; alpha-and beta-hydroxy acids; or milk protein. The active components are used in an amount that is typical for their use in any other type of composition.

It will normally be desirable to provide additional powder components to the composition, to enhance the feel of the product. The nature of the additional powder components is not limited, and can be any type of powder that acceptable for use on the skin and compatible with the other components of the composition. Examples of such powders include, but are not limited to, nylon, silica, silicone resin, polyethylene, polyurethane, boron nitride, and acrylate or methacrylate polymers or copolymers. Particularly preferred among these powders are polyurethane and silicone resins. Examples of commercially available resins of these types are BPD-500, a polyurethane(HDI/trimethylyol hexyl lactone crosspolymer), and Tospearl silicone resin (polymethylsilsesquioxane) particles, both available from Kobo Products, Inc., South Plainfield, N.J.

The powder component of the composition can also comprise spherical powders known as "soft-focus" powders. Such materials are known in the cosmetic industry for their light-scattering properties on the skin. Powders of this type may include, but are not limited to, calcium aluminum borosilicate, PMMA, polyethylene, methyl methacrylate crosspolymer, nylon-12, or ethylene/acrylic acid copolymer. The additional powder component of the composition may comprise a combination of any of the above powders. Overall, the amount and identity of the additional powder components will vary depending on the intended use and feel of the final product. Ordinarily, it will constitute from about 1–40% by weight of the total composition, preferably in the range of from 5–30%, more preferably about 10–25.

The composition can also contain pigment powders, to add color to the powder, or to constitute the pigment portion of a color cosmetic composition. The pigment powders to be used include, but are not limited to, inorganic pigments such as iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide (white), interference pigments such as micas coated with $TiO_2$, $Fe_2O_3$, or $Cr_2O_3$, zinc oxide and mixtures thereof. Also useful are transparent metal oxide-coated silica beads. Metal oxides, particularly iron and titanium oxides, are particularly preferred.

Organic pigments, however, can also be used in the compositions of the invention, provided they are not surface active; these include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed. The amount and type of pigment used in the composition will vary depending upon the nature of the final product and the desired intensity of color; generally, however, the amount of pigment, when present, will be about 1 to about 20% by weight of the total composition.

The powder compositions are prepared, in general terms, by combining all the components of the aqueous phase, including actives, if any, and the water-soluble polymer. The dry components i.e., the silica particles, additional powder components, and pigment powders, are combined and pulverized separately. The aqueous phase is then added into the dry phase and blended thoroughly. Alternatively, additional powders can be blended in at the end of the process.

In a preferred embodiment, the powder compositions of the invention are used as cosmetic, personal care, or skincare compositions. Because the compositions of the invention are substantially oil-free, i.e. contain less than about 1% of an oil component, preferably with no added oil, they are particularly useful for individuals with oily skin, and also are well-adapted for use in hot weather on any type of skin, when an oily product is particularly undesirable. In addition, the powder, upon rubbing into the skin, provides an advantageous release of a cool moisture, which can be further prolonged by the addition of menthol or other cooling materials to the formulation. Thus, because of its unique properties, the compositions provide a useful base for a variety of different types of cosmetic/skincare/personal care products.

For example, in one embodiment, the powders are used as a color cosmetic, such as an eyeshadow, blush, eyeliner or eyebrow cosmetic. These products, which for convenience traditionally are applied in powder form, in other types of formulations can gather in lines and creases, reducing the efficacy and appearance of the product. However, in the powder-to-liquid form, the liquid form of the product stays in place, is long-lasting on the skin, and is largely crease-free. It is also useful as a loose facial powder(colored or uncolored), a type of product that is frequently applied to finish the look of makeup already present on the skin. The formulations of the invention are also useful as powder-to-liquid foundation, a unique form of foundation; the product is applied as powder, which when rubbed onto the face liquefies; the liquid form on the face, due to the presence of the polymer, has long wear, and provides medium to high coverage. In a similar vein, the composition can be used as a powder makeup primer, for use over or under makeup; in both the foundation and the primer, the composition can contain antiperspirants, in addition to the natural oil absorption of the powders, to provide a drier, more comfortable, cooling, non-oily product that is particularly well-suited for use in warm weather or during exercise. A powder-to-liquid mascara as well as a powder-to-liquid, long-lasting lipstick, can also be made using the powders. Lipsticks of this type, when applied over a conventional lipstick, can convert the lipstick to a matte finish, thereby reducing the shiny appearance of the oil, and also have an anti-feathering effect.

The composition can also form the basis of a new form of deodorant/antiperspirant. Typically, deodorants are applied in stick, aerosol spray, roll-on, or cream form. Many users find one or another of these forms uncomfortable or inconvenient to apply. With the present compositions, an alternative deodorant/antiperspirant can be applied in powder form, providing the initial desirable dry feel of the powder, while providing a subsequent burst of cooling upon the release of the moisture when the product is rubbed in. Such deodorant/antiperspirant products can be conveniently applied anywhere on the body, in addition to the areas to which a deodorant/antiperspirant is normally applied, such as the underarms or the feet.

Another unique application is as a sunscreen product. Water-soluble sunscreen compounds can be readily incorporated into the water phase of the product, providing a sun product that can be applied as a powder, and which provides a desirable cool feeling upon application. Such a product may also contain an antiperspirant, which is particularly beneficial for the user sitting in the hot sun. The inclusion of a film-forming agent can cause the formulation to have an "anti-sand" effect by preventing the sand from sticking to the skin.

The powders can be applied to hair as well, acting as the base for a hair-finishing products that can contain pearlescent pigments to highlight the hair, and active agents to condition the hair. In addition, the powders can be used as would be any other powder, e.g., as a baby powder, body powder, foot powder and the like.

The powder composition can also be used as a therapeutic vehicle for pharmaceutical actives, and therefore may contain additional water-soluble therapeutic components such as agents used to treat age spots, keratoses and wrinkles, as well as analgesics, anesthetics, anti-acne agents, antibacterials, antiyeast agents, antifungal agents, antioxidants, antiviral agents, antidandruff agents, antidermatitis agents, antipruritic agents, antiemetics, antimotion sickness agents, anti-irritant agents, anti-inflammatory agents, antihyperkeratolytic agents, anti-dry skin agents, antiperspirants, antpsoriatic agents, antiseborrheic agents, hair conditioners and hair treatment agents, antiaging agents, antiwrinkle agents, sunscreen agents, antihistamine agents, skin lightening agents, depigmenting agents, wound-healing agents, vitamins, corticosteroids, self-tanning agents, or hormones.

In all cases, the powders can be applied in any way common to the use of powder compositions. For example, the powder can be applied directly to the skin or by hand after being shaken from a container; it can also be applied by brush, puff, or sponge applicator, the pressure of the applicator providing the necessary release of moisture; or it can be applied as a spray powder, and then rubbed manually into the skin.

The invention is further illustrated by the following non-limiting examples.

EXAMPLES

Example 1

This example illustrates the preparation of a powder-to-liquid foundation.

| Material | Weight percent |
| --- | --- |
| Phase I | |
| Quaternium-15 | 0.20 |
| Deionized water | 65.50 |
| Sodium dehydroacetate | 0.10 |
| Hyaluronic acid (1%) | 2.00 |
| Phase II | |
| Silica silylate | 2.70 |
| Phase III | |
| Red iron oxide | 0.14 |
| Yellow iron oxide | 0.37 |
| Black iron oxide | 0.06 |
| Titanium dioxide | 1.75 |
| HDI/trimethylol hexyl lactone crosspolymer | 14.78 |
| Phase IV | |
| polymethylsilsesquioxane | 9.00 |
| Mica/titanium dioxide/dimethicone | 2.90 |

The components of Phase I are combined at room temperature and blended to homogeneity. The components of Phases II and III are combined separately and blended in a mixer, and blended. The components of Phase I are added to the combined Phases II and III, and the blending continued until the liquid is fully incorporated into the dry ingredients. The Phase IV ingredients are then added to the mixture, which is blended to homogeneity.

Example 2

This example illustrates the preparation of an antiperspirant powder of the invention.

| Material | Weight percent |
| --- | --- |
| Phase I | |
| Quaternium-15 | 0.20 |
| Deionized water | 65.50 |
| Sodium dehydroacetate | 0.10 |
| Hyaluronic acid (1%) | 2.00 |
| Sodium polyacrylate | 0.50 |
| Aluminum zirconium tetrachlorohydrex gly | 5.00 |
| Phase II | |
| Silica silylate | 2.7 |
| Phase III | |
| Red iron oxide | 0.07 |
| Yellow iron oxide | 0.16 |
| Black iron oxide | 0.016 |
| HDI/trimethylol hexyl lactone crosspolymer | 12.054 |
| Phase IV | |
| Polymethylsilsesquioxane | 11.70 |

The ingredients are combined substantially as described in Example 1.

What we claim is:

1. A cosmetic or pharmaceutical powder-to-liquid composition comprising hydrophobically coated silica particles into which are incorporated water and a water soluble polymer, the composition containing substantially no oil.

2. The composition of claim 1 in which the silica is a fumed silica.

3. The composition of claim 1 in which the coating is covalently bonded to the particle.

4. The composition of claim 1 in which silica is a fumed silica coated with a silicone-based coating.

5. The composition of claim 4 in which the coating is an organosiloxane or a polysiloxane.

6. The composition of claim 1 in which the coating is an organosiloxane.

7. The composition of claim 1 in which the polymer is selected from the group consisting of homo- and copolymers of vinyl pyrrolidone, homo- and copolymers of vinyl alcohol, homo- or copolymers of acrylic and/or methacrylic acids, and salts and esters thereof, and polyurethanes.

8. The composition of claim 1 which comprises at least one additional powder component.

9. The composition of claim 8 in which the additional powder component is selected from the group consisting of nylon, silica, silicone resin, polyethylene, polyurethane, boron nitride, and acrylate or methacrylate polymers and copolymers.

10. The composition of claim 9 which also comprises at least one pigment component.

11. The composition of claim 1 which also comprises a water-soluble active.

12. The composition of claim 11 in which the active is a skin-conditioning agent.

13. The composition of claim 12 in which the active is an antiperspirant.

14. A cosmetic or pharmaceutical powder-to-liquid composition comprising a silicone-coated fumed silica into which is incorporated a water phase and a water-soluble polymer, and at least one additional powder component.

15. The composition of claim 14 in which the water-soluble polymer is selected from the group consisting of homo- and copolymers of vinyl pyrrolidone, homo- and copolymers of vinyl alcohol, homo- or copolymers of acrylic and/or methacrylic acids, and salts and esters thereof, and polyurethanes.

16. The composition of claim 15 in which the polymer is an acrylate polymer.

17. The composition of claim 14 in which the additional powder component is selected from the group consisting of nylon, silica, silicone resin, polyethylene, polyurethane, boron nitride, and acrylate or methacrylate polymers and copolymers.

18. The composition of claim 14 in which the silica is coated with an organosiloxane, a polysiloxane, or a silicone oil.

19. The composition of claim 18 in which the silica is coated with an organosiloxane.

20. The composition of claim 14 which also comprises a pigment.

21. The composition of claim 14 which also comprises a water soluble active.

22. The composition of claim 21 in which the active is an antiperspirant.

23. A cosmetic or pharmaceutical composition comprising an organosiloxane-coated fumed silica into which is incorporated a water phase and a water-soluble acrylate homo- or copolymer; at least one additional powder component selected from the group consisting of nylon, silica, silicone resin, polyethylene, polyurethane, boron nitride, and acrylate or methacrylate polymers and copolymers; at least one pigment, and optionally, at least one water-soluble active.

* * * * *